United States Patent [19]

Franke et al.

[11] 4,428,950

[45] Jan. 31, 1984

[54] (HETARYLPHENOXY)-(PHENYLPIPERAZINYL-PROPANOLS, THEIR PREPARATION AND DRUGS CONTAINING THESE COMPOUNDS

[75] Inventors: Albrecht Franke, Wachenheim; Gerd Steiner, Kirchheim; Peter C. Thieme, Wachenheim; Dieter Lenke, Ludwigshafen; Josef Gries, Wachenheim; Hans-Juergen Teschendorf, Ludwigshafen, all of Fed. Rep. of Germany

[73] Assignee: BASF Aktiengesellschaft, Fed. Rep. of Germany

[21] Appl. No.: 339,508

[22] Filed: Jan. 15, 1982

[30] Foreign Application Priority Data

Jan. 19, 1981 [DE] Fed. Rep. of Germany ....... 3101456

[51] Int. Cl.³ .................. C07D 403/00; A61K 31/495
[52] U.S. Cl. .................... 424/250; 544/295; 544/366; 544/370; 544/371; 544/367; 424/251
[58] Field of Search ............... 544/366, 370, 371, 367; 424/250

[56] References Cited

U.S. PATENT DOCUMENTS

| 3,577,419 | 5/1971 | Griot | 544/295 |
|---|---|---|---|
| 3,941,789 | 3/1976 | Renlh et al. | 544/370 |
| 4,134,983 | 1/1979 | Baldwin | 544/370 |

FOREIGN PATENT DOCUMENTS

| 317207 | 8/1974 | Austria | 424/250 |
|---|---|---|---|
| 2510781 | 9/1976 | Fed. Rep. of Germany | 424/273 R |
| 2926517 | 1/1981 | Fed. Rep. of Germany | 424/272 |
| 2053210 | 2/1981 | United Kingdom | 424/272 |

*Primary Examiner*—Donald G. Daus
*Assistant Examiner*—S. A. Gibson
*Attorney, Agent, or Firm*—Keil & Witherspoon

[57] ABSTRACT

Novel (hetarylphenoxy)-(phenylpiperazinyl)-propanols of the formula

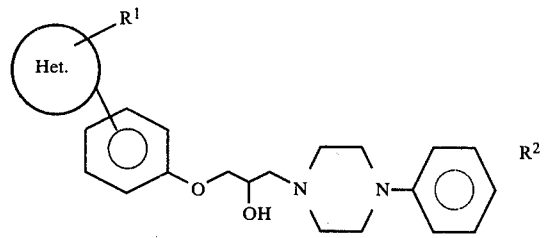

where $R^1$ is hydrogen, amino or alkyl of 1 to 4 carbon atoms, $R^2$ is hydrogen, halogen, alkyl of 1 to 4 carbon atoms or alkoxy where alkyl is of 1 to 3 carbon atoms, the phenyl ring can be monosubstituted or disubstituted by $R^2$, and the heterocyclic structure Het. is pyrimidinyl, triazol-1-yl, imidazol-1-yl, pyrazol-3-yl or isoxazol-3-yl, and their physiologically tolerated addition salts with acids, processes for their preparation, and pharmaceutical formulations which contain these compounds and exhibit predominantly hypotensive, sedative, neuroleptic and broncholytic properties.

7 Claims, No Drawings

(HETARYLPHENOXY)-(PHENYLPIPERAZINYL)-PROPANOLS, THEIR PREPARATION AND DRUGS CONTAINING THESE COMPOUNDS

The present invention relates to novel (hetarylphenoxy)-(phenylpiperazinyl)-propanols and their physiologically tolerated addition salts with acids, processes for their preparation and pharmaceutical formulations which contain these compounds and exhibit predominantly hypotensive, sedative, neuroleptic and broncholytic properties.

Patent Application No. P 30 05 287.0 describes (1,3,4-oxadiazolylphenoxy)-(phenylpiperazinyl)-propanols which exhibit a hypotensive action. This Application relates to derivatives modified by altering the heterocyclic ring, which exhibit a different profile of pharmacological action.

We have found that compounds of the general formula I

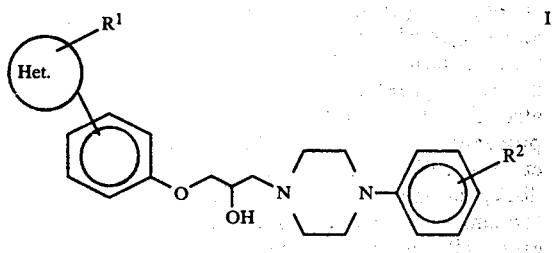

where $R^1$ is hydrogen, amino or alkyl of 1 to 4 carbon atoms, $R^2$ is hydrogen, halogen, alkyl of 1 to 4 carbon atoms or alkoxy where alkyl is of 1 to 3 carbon atoms, the phenyl ring can be monosubstituted or disubstituted by $R^2$, and the heterocyclic structure Het. is pyrimidine, triazol-1-yl, imidazol-1-yl, pyrazol-3-yl or isoxazol-3-yl, and their addition salts with acids exhibit useful pharmacological properties.

The heterocyclic structure can be in the o-, m- or p-position with respect to the ether group.

Methyl, ethyl, n-propyl, isopropyl, n-butyl and tert.-butyl are examples of straight-chain or branched alkyl $R^1$ of 1 to 4 carbon atoms.

$R^2$ can be in the o-, m- or p-position with respect to the piperazine substituent in the phenyl ring of the phenylpiperazine, and can have, for example, the following meanings: fluorine, chlorine, bromine and iodine are suitable halogen atoms, and fluorine and chlorine, in the p- or m-position, are preferred. Methoxy, ethoxy, propoxy and isopropoxy are examples of lower alkoxy, and methoxy and ethoxy in the o-position, are preferred.

Accordingly, the following are examples of novel compounds of the formula I: 1-[2-(2-aminopyrimidin-4-yl)-phenoxy]-3-[-(4-chlorophenyl)-piperazin-1-yl]-propan-2-ol, 1-[2-(2-aminopyrimidin-4-yl)-phenoxy]-3-[4-(2-methoxyphenyl)-piperazin-1-yl]-propan-2-ol, 1-[3-(2-aminopyrimidin-4-yl)-phenoxy]-3-[4-(3-chlorophenyl)-piperazin-1-yl]-propan-2-ol, 1-[3-(2-aminopyrimidin-4-yl)-phenoxy]-3-[4-(4-chlorophenyl)-piperazin-1-yl]-propan-2-ol, 1-[4-(2-aminopyrimidin-4-yl)-phenoxy]-3-[4-(3-chlorophenyl)-piperazin-1-yl]-propan-2-ol, 1-[4-(1,2,4-triazol-1-yl)-phenoxy]-3-[4-(4-fluorophenyl)-piperazin-1-yl]-propan-2-ol, 1-[4-(1,2,4-triazol-1-yl)-phenoxy]-3-[4-(3-methoxyphenyl)-piperazin-1-yl]-propan-2-ol, 1-[4-(imidazol-1-yl)-phenoxy]-3-[4-(4-fluorophenyl)-piperazin-1-yl]-propan-2-ol, 1-[2-(pyrazol-3-yl)-phenoxy]-3-[4-(4-chlorophenyl)-piperazin-1-yl]-propan-2-ol, 1-[2-(pyrazol-3-yl)-phenoxy]-3-[4-(2-methoxyphenyl)-piperazin-1-yl]-propan-2-ol, 1-[3-(pyrazol-3-yl)-phenoxy]-3-[4-(2-methoxyphenyl)-piperazin-1-yl]-propan-2-ol, 1-[3-(pyrazol-3-yl)-phenoxy]-3-[4-(3-chlorophenyl)-piperazin-1-yl]-propan-2-ol, 1-[3-(pyrazol-3-yl)-phenoxy]-3-[4-(4-chlorophenyl)-piperazin-1-yl]-propan-2-ol, 1-[4-(pyrazol-3-yl)-phenoxy]-3-[4-(3-chlorophenyl)-piperazin-1-yl]-propan-2-ol, 1-[4-(pyrazol-3-yl)-phenoxy]-3-[4-(4-chlorophenyl)-piperazin-1-yl]-propan-2-ol and 1-[2-(isoxazol-3-yl)-phenoxy]-3-[4-(2-methoxyphenyl)-piperazin-1-yl]-propan-2-ol.

Compounds of the general formula I as claimed in claim 1, where $R^1$ is hydrogen or amino and $R^2$ is fluorine, chlorine or methoxy, and their physiologically tolerated addition salts with acids are preferred.

The following compounds are particularly preferred and effective: 1-[2-(2-aminopyrimidin-4-yl)-phenoxy]-3-[4-(2-methoxyphenyl)-piperazin-1-yl]-propan-2-ol, 1-[4-(1,2,4-triazol-1-yl)-phenoxy]-3-[4-(4-fluorophenyl)-piperazin-1-yl]-propan-2-ol, 1-[4-imidazol-1-yl)-phenoxy]-3-[4-(4-fluorophenyl)-piperazin-1-yl]-propan-2-ol, 1-[2-(pyrazol-3-yl)-phenoxy]-3-[4-(2-methoxyphenyl)-piperazin-1-yl]-propan-2-ol and 1-[3-(pyrazol-3-yl)phenoxy]-3-[4-(2-methoxyphenyl)-piperazin-1-yl]-propan-2-ol.

The novel compounds, except for those with a pyrimidine radical, are obtained when a compound of the formula II

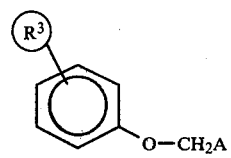

where $R^3$ is triazol-1-yl, imidazol-1-yl, pyrazol-3-yl or isoxazol-3-yl, the heterocyclic ring can be substituted by alkyl of 1 to 4 carbon atoms, and A is

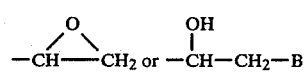

where B is a nucleofugic leaving group, is reacted in a conventional manner with a phenylpiperazine of the general formula III

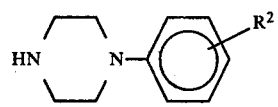

where $R^2$ has the meanings given for formula I, advantageously in a solvent and in the presence or absence of an acid acceptor, and the resulting compound of the general formula IV

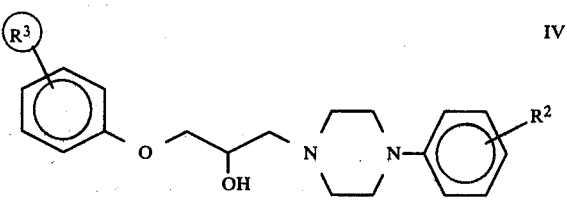

where $R^3$ has the meanings given for formula II, is converted, if appropriate, into the addition salt of a physiologically tolerated acid.

The leaving group B is preferably halogen, particularly chlorine, bromine or iodine. Further examples of suitable nucleofugic leaving groups are aromatic or aliphatic sulfonic acid esters, for example p-toluenesulfonyl, p-bromobenzenesulfonyl or methanesulfonyl.

The reactions are carried out at from 10° to 120° C., advantageously at from 50° to 120° C., under atmospheric pressure, or under superatmospheric pressure in a closed vessel, with or without heating to the above temperature range.

The starting compounds can be reacted directly, ie. without the addition of a diluent or solvent.

However, the reactions are advantageously carried out in the presence of an inert diluent or solvent, for example a lower alcohol of 1 to 4 carbon atoms, eg. methanol, ethanol or propanol, preferably isopropanol or ethanol, a lower saturated dialkyl ether, dialkyl glycol ether or cyclic ether, eg. diethyl ether, 1,2-dimethoxyethane, tetrahydrofuran or dioxane, an aromatic hydrocarbon, such as benzene or an alkylbenzene, eg. toluene or xylene, a saturated aliphatic hydrocarbon, eg. hexane, heptane or octane, a lower aliphatic ketone, eg. actone, methyl ethyl ketone or methyl isobutyl ketone, a dialkylformamide, eg. dimethylformamide or diethylformamide, or dimethylsulfoxide, or in the presence of water, or in mixtures of the above solvents.

The reaction of an epoxide of the formula II with a phenylpiperazine of the formula III is preferably carried out using a lower alcohol, in particular ethanol, propanol or isopropanol, as the solvent, and preferably at from 50° to 120° C. and under atmospheric pressure. The nucleophilic substitution of B is preferably carried out at from 90° to 120° C., using a lower aliphatic ketone, eg. acetone, diethyl ketone, methyl isopropyl ketone or methyl isobutyl ketone, a cyclic saturated ether, in particular tetrahydrofuran or dioxane, or a dialkylformamide, eg. dimethylformamide, as the solvent. The reaction is carried out in the presence or absence of a catalytic amount of sodium iodide or potassium iodide.

A mixture of the epoxide and a halohydrin may also be used as the starting compound of the formula II, since in the industrial production of the latter a mixture of this type can be formed under certain circumstances.

In an advantageous embodiment of the nucleophilic substitution of B by the phenylpiperazine derivative used, the reaction is carried out in the presence of a base as the acid acceptor. Preferred bases are alkali metal hydroxides, carbonates, bicarbonates or alcoholates, tertiary organic amines, eg. pyridine, or trialkylamines, eg. trimethylamine or triethylamine. Particularly suitable alkali metal compounds are those of sodium and potassium. The base is used in a stoichiometric amount or in slight excess. The phenylpiperazine derivative employed for the reaction may advantageously be used, in excess, also as the acid acceptor.

The overall reaction is complete in general in the course of from 2 to 15 hours, depending on the reaction temperature. The product can be obtained in a conventional manner, for example by filtration or by distilling off the diluent or solvent from the reaction mixture, and can be purified in a conventional manner, for example by recrystallization from a solvent, conversion to an addition compound with an acid, or column chromatography.

The starting compounds of the formula (II) are obtained when a phenol of the general formula V

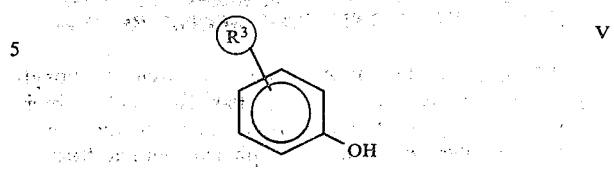

where $R^3$ has the meanings given for formula II, is alkylated with an epihalohydrin or an α,ω-dihalopropan-2-ol.

Epichlorohydrin, epibromohydrin and epiiodohydrin are suitable epihalohydrins, and 1,3-dichloropropan-2-ol and 1,3-dibromopropan-2-ol are particularly suitable α,ω-dihalopropan-2-ols.

The alkylation of the phenol derivatives of the formula V for the preparation of the starting compounds of the formula II is advantageously carried out at from 0° to 120° C., under atmospheric pressure, or under superatmospheric pressure in a closed vessel. The reaction is advantageously carried out in an inert diluent or solvent, for example a lower aliphatic ketone, eg. acetone, methyl ethyl ketone or methyl isobutyl ketone, a lower alcohol of 1 to 4 carbon atoms, eg. methanol, ethanol, propanol or butanol, a saturated aliphatic or cyclic ether, eg. dialkyl ether, tetrahydrofuran or dioxane, a dialkylformamide, eg. dimethylformamide or diethylformamide, or hexamethylphosphorotriamide, or with excess alkylating agent as the diluent or solvent.

The reaction is preferably carried out in the presence of a base as the acid acceptor. Suitable bases are alkali metal carbonates, bicarbonates, hydroxides, hydrides or alcoholates, in particular those of sodium and potassium, basic oxides, eg. aluminum oxide or calcium oxide, tertiary organic bases, eg. pyridine, or lower trialkylamines, eg. trimethylamine or triethylamine. The base can be used in a catalytic or stoichiometric amount or in slight excess, based on the alkylating agent employed.

The phenol derivatives are preferably reacted with epibromohydrin or 1,2-dibromopropan-2-ol in a solvent mixture consisting of an ether and a polar aprotic solvent, in particular tetrahydrofuran and hexamethylphosphorotriamide, at from 0° to 50° C.

Furthermore, the starting compounds of the formula II can be converted into one another by simple acid/base reaction. Thus, a 2,3-epoxypropoxyphenyl derivative can be converted using the appropriate hydrohalic acid into a 2-hydroxy-3-halopropoxyphenyl derivative, and in addition to conventional solvents, an aliphatic or cyclic ether, eg. diethyl ether, tetrahydrofuran or dioxane, or a lower alcohol, eg. methanol, ethanol or propanol, is used as the diluent or solvent.

The 2-hydroxy-3-halopropoxyphenyl derivatives can also be converted into 2,3-epoxypropoxyphenyl derivatives using a base, for example an alkali metal hydroxide, carbonate, bicarbonate, alcoholate or hydride, a tertiary organic amine, eg. pyridine, a tertiary aliphatic amine, in particular trimethylamine or triethylamine, or piperidine. These reactions can be carried out at room temperature, or can be accelerated or brought to completion by heating, for example at from 60° to 120° C.

The reaction can be carried out under atmospheric pressure, or under superatmospheric pressure in a closed vessel, with or without simultaneous heating. The starting materials for this conversion can be isolated beforehand or produced in the reaction mixture and directly processed further, without subsequent isolation and purification.

The phenol derivatives employed as the starting compounds of the formula V are known from the literature (German Laid-Open Application DOS Nos. 2,803,870 and DOS 2,510,781, and J. Org. Chem. 42 (1977), 1356–1360) or are available commercially.

The novel compounds of the general formula I, where

is 2-aminopyrimidin-4-yl, pyrazol-3-yl or isoxazol-3-yl, are obtained when a 1-[(3-dialkylamino-1-oxopropenyl)-phenoxy]-(phenylpiperazin-1-yl)-propan-2-ol derivative of the general formula VI

VI

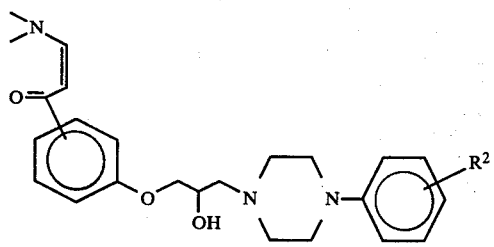

is reacted in a conventional manner with guanidine, hydroxylamine or hydrazine hydrate, advantageously in the presence of a polar solvent, with or without the addition of a base, at from 50° to 120° C., and the resulting compound of the general formula I with 2-aminopyrimidin-4-yl, isoxazol-3-yl or pyrazol-3-yl for

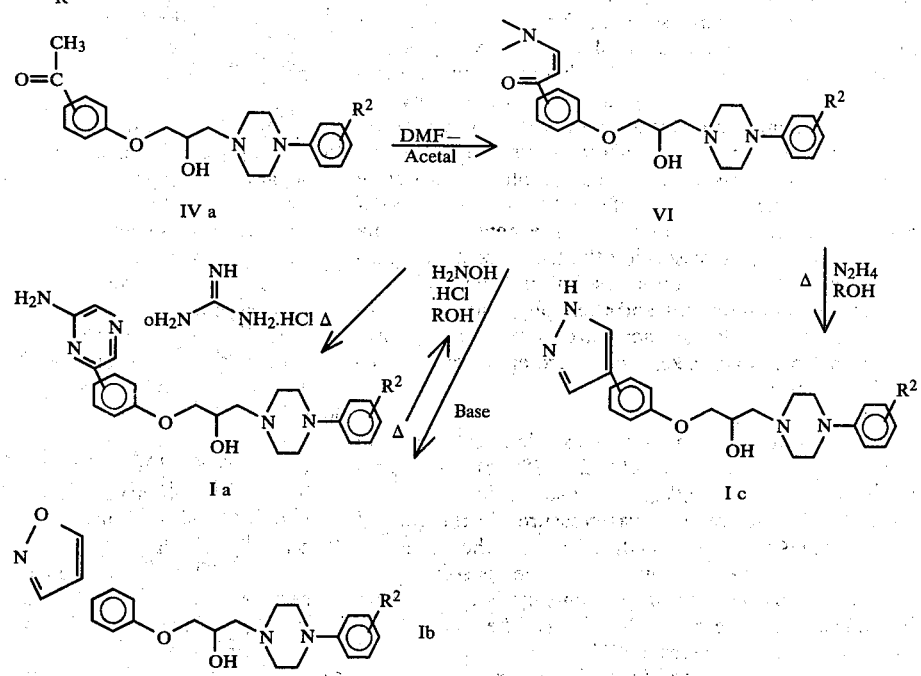

is converted, if appropriate, into the addition salt of a physiologically tolerated acid.

The reaction is represented by the following equation. The compounds of the formula VI are obtained, for example, by reacting the appropriate carbonylmethyl compounds with dimethylformamide acetal, as shown in the equation. Dimethylamino and diethylamino are suitable dialkylamino groups for the oxopropenyl radical.

The acetophenone derivative IVa is reacted with dimethylformamide acetal in a polar solvent, for example a lower alcohol, preferably ethanol, at from 50° to 120° C., under atmospheric pressure, to give the corresponding 1-[(3-dialkylamino-1-oxopropenyl)-phenoxy]-(phenylpiperazin-1-yl)-propan-2-ol of the general formula VI. The reactions are normally complete after from 3 to 8 days.

The 1-[(3-alkylamino-1-oxopropenyl)-phenoxy]-(phenylpiperazin-1-yl)-propan-2-ol derivative VI is then reacted with guanidine, hydroxylamine or hydrazine hydrate to give the corresponding end products of the general formula Ia, Ib or Ic. The reactions are advantageously carried out in the presence of a polar solvent, for example a lower alcohol, preferably ethanol, with or without the addition of a base, for example an alkali metal alcoholate, preferably sodium methylate, at from 50° to 120° C., and are normally complete after from 1 to 10 days.

The novel compounds of the formula (I) have a center of chirality at the 2nd carbon atom of the aliphatic side chain and are obtained as racemic mixtures, which can be separated into the optically active antipodes by conventional methods, for example by the formation of diastereomeric salts with optically active acids, eg. dibenzoyltartaric acid, campher-10-sulfonic acid, ditoluyltartaric acid or 3-bromocampher-8-sulfonic acid.

The novel compound obtained may be converted into the addition salt of a physiologically tolerated acid. Examples of customary physiologically tolerated inorganic acids are hydrochloric acid, hydrobromic acid, phosphoric acid or sulfuric acid, and examples of organic acids are oxalic acid, maleic acid, fumaric acid, lactic acid, tartaric acid, malic acid, citric acid, salicylic acid, adipic acid or benzoic acid, or others which are described in Fortschritte der Arzneimittelforschung Volume 10 (1966), 224–225, Birkhäuser Verlag, Basel and Stuttgart.

As a rule, the acid addition salts are obtained in a conventional manner by mixing the free base, or a solution thereof, with the appropriate acid, or a solution thereof, in an organic solvent, for example a lower alcohol, eg. methanol, ethanol or propanol, a lower ketone, eg. acetone methyl ethyl ketone or methyl isobutyl ketone, or an ether, eg. diethyl ether, tetrahydrofuran or dioxane. In order to facilitate the precipitation of crystals, mixtures of the above solvents can also be used. It is also possible to prepare a pharmaceutically acceptable aqueous solution of an addition compound of a phenylpiperazinyl derivative of the general formula (I) with an acid, by dissolving the free base of the general formula (I) in an aqueous solution of an acid.

The novel compounds and their physiologically tolerated addition salts with acids are useful as drugs having a hypotensive, sedative, neuroleptic and broncholytic action.

Hypotensive action:

The hypotensive action was demonstrated on Sprague-Dawley rats (weight: 230–280 g) under urethane narcosis (1.78 g/kg, administered intraperitoneally). The blood pressure was measured in the carotid artery. The substance was administered either by introduction into a jugular vein (as an aqueous solution, at the rate of 1 ml/kg) or intraperitoneally as a suspension in tragacanth (at the rate of 10 ml/kg). The ED 20%, ie. the dose which produces a 20% lowering of the blood pressure, was determined from the linear regression of log dose (mg/kg) and relative lowering of the blood pressure ($\Delta\%$).

Sedative action:

The substance was administered orally to 4–8 groups each comprising 3 female NMRI mice. The orientation hypermotility induced by a new environment is determined photoelectrically, 30 minutes after administration of the substance, over a period of 30 minutes. The ED 50%, ie. the dose which produces a 50% reduction in orientation hypermotility compared to placebo-treated control animals, is determined.

Cataleptic action:

30, 60, 120 and 240 minutes after intraperitoneal administration of the substance, female Sprague-Dawley rats were placed with the front extremities on an 8 cm high bar. If, because of postural rigidity, the animals remain in this position for longer than 15 seconds, they are regarded as cataleptic. The frequency of cataleptic reaction per dose (n/dose=10) is determined, and the ED 50%, ie. the dose at which 50% of the animals are cataleptic, is found by Probit analysis.

Broncholytic action:

Male or female guineapigs (Pirbright white, weight 300–500 g) under urethane narcosis (1.5 g/kg administered intraperitoneally) are subjected to artificial respiration using a tracheal cannula. Bronchospasms are caused by intravenous injection of histamine dihydrochloride (1.0–4.64 μg/kg), and an antagonistic effect on these can be brought about by prior intravenous administration of the test substance. The spasms are recorded by the method of Konzett and Rössler (Naunyn Schmiedeberg's Arch. 195 (1940), 71), via inductive pressure sensors.

According to the results summarized in Table 1, the compounds of Examples 2 and 3 exhibit powerful sedative-neuroleptic properties. The effect in respect of sedation is, respectively, 84 and 77% of that of chlorpromazine, whilst the effect in respect of catalepsy is, respectively, 43 and 20% of that of chlorpromazine. Taking into account the hypotensive effect—a property which is an undesirable side effect in sedatives/neuroleptics—the compounds are clearly superior to chlorpromazine. The quotient of the sedative effective dose and the hypotensive effective dose is respectively 10 and 43 times more advantageous than for chlorpromazine.

Others amongst the novel compounds possess, on the one hand, a particularly pronounced hypotensive action and, on the other hand, a comparatively weak sedative action (Table 2). Thus, the compounds of Examples 10, 5 and 15 have a hypotensive action at lower doses than chlorpromazine. The sedative side-effect is only observed at doses which are roughly 400–1,300 times greater (whilst for chlorpromazine they are 80 and 13 times greater).

The compound of Example 1 shows a relatively slight sedative action coupled with a strong broncholytic effect on the histamine bronchospasm of the guineapig. 0.1 mg/kg administered intravenously inhibit the spasm by an average of 87%. The sedative effect (ED 50%=7.6 mg/kg) is only 28% of the effect of chlorpromazine.

TABLE 1

| Compound of Example No. | Sedative effect[1] ED 50% | R.A.[4] | Cataleptic effect[2] ED 50% | R.A.[4] | Hypotensive effect[3] ED 20% | R.A.[4] | Q[5] |
|---|---|---|---|---|---|---|---|
| 2 | 2.52 | 0.84 | 10.0 | 0.43 | 0.316 i.v. | 0.08 | 8.0 |
| 3 | 2.75 | 0.77 | 21.5 | 0.2 | 10.0 i.p. | 0.02 | 0.3 |
| chlorpromazine | 2.11 | 1.0 | 4.3 | 1.0 | 0.026 i.v. | 1.0 | 81.1 |
|  |  |  |  |  | 0.164 i.p. | 1.0 | 12.9 |

[1]Mouse, oral administration
[2]Rat, intraperitoneal administration
[3]Rat, intravenous (i.v.) or intraperitoneal (i.p.) administration
[4]Relative activity; chlorpromazine = 1.00.
[5]$Q = \dfrac{\text{ED 50\% for sedative effect}}{\text{ED 20\% for hypotensive effect}}$

TABLE 2

| Compound of Example No. | Hypotensive effect ED 20%[1] | R.A.[2] | Sedative effect ED 50%[3] | R.A.[2] | Q[4] |
|---|---|---|---|---|---|
| 10 | 0.0328 i.v. | 0.79 | 14.5 | 0.15 | 442 |
| 5 | 0.0795 i.p. | 2.06 | 32.8 | 0.06 | 413 |
| 15 | 0.0187 i.v. | 1.39 | 25.1 | 0.08 | 1,342 |
| chlor- | 0.0260 i.v. | 1.00 | 2.11 | 1.00 | 81 |

TABLE 2-continued

| Compound of Example No. | Hypotensive effect ED 20%[1] | R.A.[2] | Sedative effect ED 50%[3] | R.A.[2] | Q[4] |
|---|---|---|---|---|---|
| promazine | 0.164 i.p. | 1.00 | 2.11 | 1.00 | 13 |

[1]Dose which reduces the blood pressure by 20% (rat, i.v. or i.p.)
[2]Relative activity; chlorpromazine = 1.00
[3]Dose which reduces the motility by 50% (mouse, oral administration)
[4]$Q = \frac{ED\ 50\%\ for\ sedative\ effect}{ED\ 20\%\ for\ hypotensive\ effect}$ Accordingly, the present invention also relates to drugs or formulations which in addition to conventional carriers and diluents contain a compound of the formula I, or a physiologically tolerated addition salt thereof with an acid, as the active compound, and to the use of the novel compounds in the treatment of hypretonia, psychic disorders, insomnia or bronchial disorders.

The novel compounds may be employed in the conventional solid or liquid pharmaceutical forms, such as tablets, capsules, powders, granules, coated tablets or solutions. These are prepared in a conventional manner, and to do so the active compounds can be mixed with the conventional pharmaceutical auxiliaries, such as talc, gum arabic, sucrose, lactose, cereal starch or corn starch, potato flour, magnesium stearate, alginates, gum tragacanth, carraghenates, polyvinyl alcohol, polyvinylpyrrolidone, aqueous or non-aqueous carriers, wetting agents, dispersants, emulsifiers and/or preservatives (cf. L. G. Goodman and A. Gilman, The Pharmacological Basis of Therapeutics). The formulations thus obtained normally contain from 0.001 to 99% by weight of the active compound.

The preferred formulations are those suitable for oral administration. Examples of these are tablets, film tablets, coated tablets, capsules, pills, powders, solutions, suspensions and depot forms. Parenteral formulations, such as injection solutions, may also be used. Suppositories are a further example of suitable formulations.

Appropriate tablets may be obtained, for example, by mixing the active compounds with conventional auxiliaries, for example inert diluents, such as dextrose, sugar, sorbitol, mannitol, polyvinylpyrrolidone, calcium carbonate, calcium phosphate or lactose, disintegrating agents, such as corn starch or alginic acid, binders, such as starch or gelatin, lubricants, such as magnesium stearate or talc, and/or agents for achieving a depot effect, such as carboxypolymethylene, carboxymethylcellulose, cellulose acetate phthalate or polyvinyl acetate. The tablets can also consist of a plurality of layers.

Correspondingly, coated tablets can be prepared by coating cores, prepared similarly to the tablets, with agents conventionally used in tablet coatings, for example collidone or shellac, gum arabic, talc, titanium dioxide or sugar. The coating can also consist of a plurality of layers, and the auxiliaries mentioned above in connection with tablets may be used therein.

Solutions or suspensions containing the novel active compounds may additionally contain flavor improvers, such as vanillin or orange extract. They may also contain suspending agents, such as sodium carboxymethylcellulose, or preservatives, such as p-hydroxybenzoates. Capsules containing the active compounds may be prepared, for example, by mixing the active compound with an inert carrier, such as lactose or sorbitol, and encapsulating the mixture in gelatin capsules. Suitable suppositories can be prepared, for example, by mixing the active compounds with appropriate carriers, such as neutral fats or polyethylene glycol or their derivatives.

The dosage of the compounds according to the invention depends on the age, condition and weight of the patient and on the route of administration. As a rule, the daily dose of active compound is from 5 to 100, preferably from 10 to 80, mg.

The Examples which follow illustrate the invention.

EXAMPLE 1

1-[4-(1,2,4-Triazol-1-yl)-phenoxy]-3-[4-(3-methoxyphenyl)-piperazin-1-yl]-propan-2-ol (a) 3.0 g (0.014 mole) of 2,3-epoxypropoxy-4-(1,2,4-triazol-1-yl)-benzene and 2.7 g (0.014 mole) of 1-(2-methoxyphenyl)-piperazine in 60 ml of isopropanol are refluxed for from 10 to 17 hours. The solvent is stripped off in a rotary evaporator, the oily residue is taken up in methylene chloride, the solution is dried over anhydrous sodium sulfate, the latter is filtered off, and the filtrate is concentrated.

The oily residue is taken up in ether and the resulting precipitate is filtered off under suction and washed with ether. 2.4 g (42%) of product of melting point 145°–146° C. are obtained.

(b) The intermediate 2,3-epoxypropoxy-4-(1,2,4-triazol-1-yl)-benzene is prepared in the following manner: 2.9 g (0.067 mole) of sodium hydride, as a 55% strength suspension in liquid paraffin, are introduced into 70 ml of anhydrous tetrahydrofuran, and a solution of 10.8 g (0.067 mole) of 4-(1,2,4-triazol-1-yl)-phenol in 50 ml of tetrahydrofuran is added dropwise. 9.2 g (0.067 mole) of epibromohydrin are then added dropwise. The reaction mixture is stirred for from 5 to 10 hours at room temperature and then poured onto 500 ml of aqueous sodium chloride solution, and the precipitate which separates out is filtered off under suction and washed thoroughly with water. The crude product is recrystallized from toluene/petroleum ether. 11.2 g (77%) of product of melting point 104°–105° C. are isolated.

EXAMPLE 2

1-[4-(1,2,4-Triazol-1-yl)-phenoxy]-3-[4-(4-fluorophenyl)-piperazin-1-yl]-propan-2-ol The preparation is carried out as described in Example 1a, using 1-(4-fluorophenyl)-piperazine. The crude product crystallizes out from the cooled reaction mixture, which is left to stand overnight, and is recrystallized from isopropanol. Yield 74%, melting point 149°–150° C.

EXAMPLE 3

1-[4-(Imidazol-1-yl)-phenoxy]-3-[4-(4-fluorophenyl)-piperazin-1-yl]-propan-2-ol (a) The preparation is carried out as described in Example 1a, using 2,3-epoxypropoxy-4-(imidazol-1-yl)-benzene and 1-(4-fluorophenyl)-piperazine. The crude product is most appropriately purified by column chromatography (silica gel, mobile phase methylene chloride/methanol 95/5), followed by recrystallization from ethanol, with the addition of active charcoal. Yield 51%, melting point 144°–146° C.

(b) The intermediate 2,3-epoxypropoxy-4-(imidazol-1-yl)-benzene is obtained as described in Example 1b, using 4-(imidazol-1-yl)-phenol. The reaction mixture is poured onto sodium chloride solution and extracted several times with methylene chloride. The organic phase is worked up in the conventional manner and the product is isolated as an oil which is sufficiently pure for further reaction.

EXAMPLE 4

1-[2-(2-Aminopyrimidin-4-yl)-phenoxy]-3-[4-(4-chlorophenyl)-piperazin-1-yl]-propan-2-ol (a)

1-[2-Carbonylmethyl-phenoxy]-3-[4-(4-chlorophenyl)-piperazin-1-yl]-propan-2-ol.HCl 26.0 g of 1-(4-chlorophenyl)-piperazine are added to 25.0 g (0.13 mole) of 2-(2,3-epoxypropoxy)-acetophenone in 100 ml of propanol, and the mixture is refluxed for from 4 to 8 hours. The solvent is distilled off, the residue is taken up in a little ethanol and converted into the hydrochloride with ethereal hydrochloric acid, and the hydrochloride is recrystallized from ethanol/ether. 33.9 g (61%) of product of melting point 186° C. are isolated.

(b)

1-[2-(3-Dimethylamino-1-oxo-propenyl)-phenoxy]-3-[4-(4-chlorophenyl)-piperazin-1-yl]-propan-2-ol.HCl 20 ml of dimethylformamide dimethyl acetal are added to 27.0 g (0.064 mole) of 1-(2-carbonylmethyl-phenoxy)-3-[4-(4-chlorophenyl)-piperazin-1-yl]-propan-2-ol.HCl in 250 ml of absolute ethanol, the mixture is refluxed for 60 hours and then concentrated under reduced pressure, several portions of methanol are added to the oily residue and the solution is again concentrated. The resulting crude product (26.5 g, 86%) is sufficiently pure for further reaction.

(c)

1-[2-(2-Aminopyrimidin-4-yl)-phenoxy]-3-[4-(4-chlorophenyl)-piperazin-1-yl]-propan-2-ol 2.0 g (0.021 mole) of guanidine hydrochloride and 0.042 mole of a 30% strength sodium methylate solution are added to 10.0 g (0.021 mole) of 1-[2-(3-dimethylamino-1-oxo-propenyl)-phenoxy]-3-[4-(4-chlorophenyl)-piperazin-1-yl]-propan-2-ol.HCl in 250 ml of ethanol, and the mixture is refluxed for 12 hours. The hot solution is filtered and the filtrate is concentrated. The crude product is recrystallized from ethanol, and 3.5 g (38%) of product of melting point 159°–160° C. are isolated.

EXAMPLE 5

1-[2-(2-Aminopyrimidin-4-yl)-phenoxy]-3-[4-(2-methoxyphenyl)-piperazin-1-yl]-propan-2-ol (a)

1-(2-Carbonylmethylphenoxy)-3-[4-(2-methoxyphenyl)-piperazin-1-yl]-propan-2-ol

The preparation is carried out as described in Example 4a, using 1-(2-methoxyphenyl)-piperazine. The hydrochloride is reconverted into the free base of melting point 116°–118° C. by adding 2 N sodium hydroxide solution and extracting with methylene chloride. Yield 75%.

(b)

1-[2-(3-Dimethylamino-1-oxo-propenyl)-phenoxy]-3-[4-(2-methoxyphenyl)-piperazin-1-yl]-propan-2-ol The preparation is carried out as described in Example 4b, using 1-(2-carbonylmethylphenoxy)-3-[4-(2-methoxyphenyl)-piperazin-1-yl]-propan-2-ol and refluxing for 8 days. The product is an oil (yield 83%).

(c)

1-[2-(2-Aminopyrimidin-4-yl)-phenoxy]-3-[4-(2-methoxyphenyl)-piperazin-1-yl]-propan-2-ol The preparation is carried out as described in Example 4c, using 1-[2-(3-dimethylamino-1-oxo-propenyl)-phenoxy]-3-[4-(2-methoxyphenyl)-piperazin-1-yl]-propan-2-ol and refluxing for 8 days. A product of melting point 147°–149° C. is obtained (yield 57%).

EXAMPLE 6

1-[3-(2-Aminopyrimidin-4-yl)-phenoxy]-3-[4-(3-chlorophenyl)-piperazin-1-yl]-propan-2-ol (a)

1-(3-Carbonylmethylphenoxy)-3-[4-(3-chlorophenyl)-piperazin-1-yl]-propan-2-ol.HCl The preparation is carried out as described in Example 4a, using 3-(2,3-epoxypropoxy)-acetophenone and 1-(3-chlorophenyl)-piperazine. A product of melting point 232°–233° C. is obtained (yield 65%).

(b)

1-[3-(3-Dimethylamino-1-oxo-propenyl)-phenoxy]-3-[4-(3-chlorophenyl)-piperazin-1-yl]-propan-2-ol.HCl The preparation is carried out as described in Example 4b, using 1-(3-carbonylmethylphenoxy)-3-[4-(3-chlorophenyl)-piperazin-1-yl]-propan-2-ol.HCl, and the product is obtained in 85% yield.

(c)

1-[3-(2-Aminopyrimidin-4-yl)-phenoxy]-3-[4-(3-chlorophenyl)-piperazin-1-yl]-propan-2-ol The preparation is carried out as described in Example 4c, using 1-[3-(3-dimethylamino-1-oxo-propenyl)-phenoxy]-3-[4-(3-chlorophenyl)-piperazin-1-yl]-propan-2-ol.HCl and refluxing for 2 days. A product of melting point 140°–141° C. is obtained (yield 32%).

EXAMPLE 7

1-[3-(2-Aminopyrimidin-4-yl)-phenoxy]-3-[4-(4-chlorophenyl)-piperazin-1-yl]-propan-2-ol (a)

1-(3-Carbonylmethylphenoxy)-3-[4-(4-chlorophenyl)-piperazin-1-yl]-propan-2-ol

The preparation is carried out as described in Example 4a, using 3-(2,3-epoxypropoxy)-acetophenone and 1-(4-chlorophenyl)-piperazine. After the reaction mixture has cooled, the product crystallizes out and is filtered off under suction and recrystallized from propanol, with the addition of active charcoal. Yield 83%.

(b)

1-[3-(3-Dimethylamino-1-oxo-propenyl)-phenoxy]-3-[4-(4-chlorophenyl)-piperazin-1-yl]-propan-2-ol The preparation is carried out as described in Example 4b, using 1-[3-carbonylmethylphenoxy)-3-[4-(4-chlorophenyl)-piperazin-1-yl]-propan-2-ol. After the reaction mixture has cooled, the precipitate is filtered off under suction and recrystallized from ethanol. A product of melting point 144°–145° C. is obtained (yield 76%).

(c)
1-[3-(2-Aminopyrimidin-4-yl)-phenoxy]-3-[4-(4-chlorophenyl)-piperazin-1-yl]-propan-2-ol The preparation is carried out as described in Example 4c, using 1-[3-(3-dimethylamino-1-oxo-propenyl)-phenoxy]-3-[4-(4-chlorophenyl)-piperazin-1-yl]-propan-2-ol and refluxing for 10 days. A product of melting point 141°–142° C. is obtained (yield 49%).

EXAMPLE 8
1-[4-(2-Aminopyrimidin-4-yl)-phenoxy]-3-[4-(3-chlorophenyl)-piperazin-1-yl]-propan-2-ol

(a)
1-[4-Carbonylmethylphenoxy]-3-[4-(3-chlorophenyl)-piperazin-1-yl]-propan-2-ol The preparation is carried out as described in Example 4a, using 4-(2,3-epoxypropoxy)-acetophenone. The solvent is distilled off, the residue is recrystallized from ethanol, and a product of melting point 106°–107° C. is obtained (yield 89%).

(b)
1-[4-(3-Dimethylamino-1-oxo-propenyl)-phenoxy]-3-[4-(3-chlorophenyl)-piperazin-1-yl]-propan-2-ol The preparation is carried out as described in Example 4b, using 1-(4-carbonylmethylphenoxy)-3-[4-(3-chlorophenyl)-piperazin-1-yl]-propan-2-ol and refluxing for 10 days. The reaction mixture is cooled, and the precipitate is filtered off under suction and recrystallized from ethanol. A product of melting point 130°–133° C. is obtained (yield 63%).

(c)
1-[4-(2-Aminopyrimidin-4-yl)-phenoxy]-3-[4-(3-chlorophenyl)-piperazin-1-yl]-propan-2-ol The preparation is carried out as described in Example 4c, using 1-[4-(3-dimethylamino-1-oxo-propenyl)-phenoxy]-3-[4-(3-chlorophenyl)-piperazin-1-yl]-propan-2-ol and refluxing for 4 days. A product of melting point 197°–198° C. is obtained (yield 35%).

EXAMPLE 9
1-[2-(Pyrazol-3-yl)-phenoxy]-3-[4-(4-chlorophenyl)-piperazin-1-yl]-propan-2-ol 15 ml of hydrazine hydrate are added to 8.0 g (0.017 mole) of 1-[2-(3-Dimethylamino-1-oxo-propenyl)-phenoxy]-3-[4-(4-chlorophenyl)-piperazin-1-yl]-propan-2-ol.HCl (Example 4b) in 100 ml of ethanol, and the mixture is refluxed for 3 days. The solvent is distilled off and the residue is recrystallized from ethanol. 6.2 g (88%) of a product of melting point 120°–121° C. are isolated.

EXAMPLE 10
1-[2-(Pyrazol-3-yl)-phenoxy]-3-[4-(2-methoxyphenyl)-piperazin-1-yl]-propan-2-ol.HCl The preparation is carried out as described in Example 9, using 1-[2-(3-dimethylamino-1-oxo-propenyl)-phenoxy]-3-[4-(2-methoxyphenyl)-piperazin-1-yl]-propan-2-ol (Example 5b) and reducing the reaction time to 4 hours. The solvent is distilled off, the residue is dissolved in methylene chloride, and the organic phase is washed several times with water, dried and concentrated. The residue is converted into the hydrochloride using ethereal hydrochloric acid and is recrystallized from ether/ethanol. A product of melting point 134°–135° C. is obtained (yield 46%).

EXAMPLE 11
1-[3-(Pyrazol-3-yl)-phenoxy]-3-[4-(3-chlorophenyl)-piperazin-1-yl]-propan-2-ol The preparation is carried out as described in Example 9, using 1-[3-(3-dimethylamino-1-oxo-propenyl)-phenoxy]-3-[4-(3-chlorophenyl)-piperazin-1-yl]-propan-2-ol.HCl (Example 6b), and a product of melting point 154°–156° C. is obtained (yield 68%).

EXAMPLE 12
1-[3-(Pyrazol-3-yl)-phenoxy]-3-[4-(4-chlorophenyl)-piperazin-1-yl]-propan-2-ol The preparation is carried out as described in Example 9, using 1-[3-(3-dimethylamino-1-oxo-propenyl)-phenoxy]-3-[4-(4-chlorophenyl)-piperazin-1-yl]-propan-2-ol (Example 7b) and increasing the reaction time to 10 days. A product of melting point 152°–153° C. is obtained (yield 31%).

EXAMPLE 13
1-[4-(Pyrazol-3-yl)-phenoxy]-3-[4-(3-chlorophenyl)-piperazin-1-yl]-propan-2-ol The preparation is carried out as described in Example 9, using 1-[4-(3-dimethylamino-1-oxo-propenyl)-phenoxy]-3-[4-(3-chlorophenyl)-piperazin-1-yl]-propan-2-ol (Example 8b) and increasing the reaction time to 5 days. A product of melting poing 189°–190° C. is obtained (yield 54%).

EXAMPLE 14
1-[4-(Pyrazol-3-yl)-phenoxy]-3-[4-(4-chlorophenyl)-piperazin-1-yl]-propan-2-ol

(a)
1-(4-Carbonylmethylphenoxy)-3-[4-(4-chlorophenyl)-piperazin-1-yl]-propan-2-ol The preparation is carried out as described in Example 4a, using 4-(2,3-epoxypropoxy)-acetophenone and 1-(4-chlorophenyl)-piperazine. The reaction mixture is cooled, and the precipitate crude product is filtered off under suction and recrystallized from ethanol/dimethylformamide. A product of melting point 154° C. is obtained (yield 74%).

(b)
1-[4-(3-Dimethylamino-1-oxo-propenyl)-phenoxy]-3-[4-(4-chlorophenyl)-piperazin-1-yl]-propan-2-ol The preparation is carried out as described in Example 4b, using 1-(4-carbonylmethylphenoxy)-3-[4-(4-chlorophenyl)-piperazin-1-yl]-propan-2-ol and increasing the reaction time to 60 days. The reaction mixture is cooled, and the precipitate crude product is filtered off under suction and recrystallized from ethanol/dimethylformamide. A product of melting point 185° C. is obtained (yield 47%).

(c)
1-[4-(Pyrazol-3-yl)-phenoxy]-3-[4-(4-chlorophenyl)-piperazin-1-yl]-propan-2-ol The preparation is carried out as described in Example 9, using 1-[4-(3-dimethylamino-1-oxo-propenyl)-phenoxy]-3-[4-(4-chlorophenyl)-piperazin-1-yl]-propan-2-ol and decreasing the reaction time to 1 day. A product of melting point 211°–212° C. is obtained (yield 69%).

EXAMPLE 15

1-[3-(Pyrazol-3-yl)-phenoxy]-3-[4-(2-methoxyphenyl)-piperazin-1-yl]-propan-2-ol.3HCl (a)
1-(3-Carbonylmethylphenoxy)-3-[4-(2-methoxyphenyl)-piperazin-1-yl]-propan-2-ol.2HCl The preparation is carried out as described in Example 4a, using 4-(2,3-epoxypropoxy)-acetophenone and 1-(2-methoxyphenyl)-piperazine. A product which decomposes at 206° C. is obtained (yield 65%). The free base can be extracted from an aqueous alkaline solution of the product using methylene chloride.

(b)
1-[3-(3-Dimethylamino-1-oxo-propenyl)-phenoxy]-3-[4-(2-methoxyphenyl)-piperazin-1-yl]-propan-2-ol The preparation is carried out as described in Example 4b, using 1-(3-carbonylmethylphenoxy)-3-[4-(2-methoxyphenyl)-piperazin-1-yl]-propan-2-ol (free base). The reaction mixture is cooled, and the precipitated crude product is filtered off under suction and recrystallized from ethanol/dimethylformamide. A product of melting point 131° C. is obtained (yield 34%).

(c)
1-[3-(Pyrazol-3-yl)-phenoxy]-3-[4-(2-methoxyphenyl)-piperazin-1-yl]-propan-2-ol.3HCl The preparation is carried out as described in Example 9, using 1-[3-(3-dimethylamino-1-oxo-propenyl)-phenoxy]-3-[4-(2-methoxyphenyl)-piperazin-1-yl]-propan-2-ol. The solvent is distilled off, and the residue is converted into the hydrochloride using ethereal hydrochloric acid and is recrystallized from ether/ethanol. A product of melting point 233°–234° C. is obtained (yield 78%).

EXAMPLE 16

1-[2-(Isoxazol-3-yl)-phenoxy]-3-[4-(2-methoxyphenyl)-piperazin-1-yl]-propan-2-ol.2HCl (a) 6.0 g (0.028 mole) of 2,3-epoxypropoxy-2-(isoxazol-3-yl)-benzene and 5.4 g (0.028 mole) of 1-(2-methoxyphenyl)-piperazine in 100 ml of n-propanol are refluxed for 10 hours. The solvent is distilled off, and the residue is converted into the hydrochloride using ethereal hydrochloric acid. The hydrochloride is recrystallized from methanol/acetone/ether to give 7.9 g (59%) of a product of melting point 210°–212° C.

(b) The intermediate 2,3-epoxypropoxy-2-(isoxazol-3-yl)-benzene is prepared in the following manner:

3.0 g (0.069 mole) of sodium hydride, as a 55% strength suspension in liquid paraffin, are introduced into 100 ml of anhydrous tetrahydrofuran, and 10.0 g (0.062 mole) of 2-(isoxazol-3-yl)-phenol dissolved in 50 ml of tetrahydrofuran and 50 ml of hexamethylphosphorotriamide are added dropwise, followed by the dropwise addition of 17 g (0.124 mole) of epibromohydrin.

The reaction mixture is stirred for from 5 to 10 hours at room temperature, poured onto 500 ml of aqueous sodium chloride solution and extracted several times with ether. The organic phase is dried and concentrated, and the crude product is obtained as an oil which partially crystallizes. The crystals are filtered off under suction and washed with a little ether. 6.4 g (48%) of a product of melting point 64°–67° C. are isolated.

Examples of pharmaceutical formulations:

| Examples of tablets | | |
| --- | --- | --- |
| 1. | An active compound of formula I | 10 mg |
| | Lactose | 200 mg |
| | Methylcellulose | 15 mg |
| | Corn starch | 50 mg |
| | Talc | 11 mg |
| | Magnesium stearate | 4 mg |
| 2. | An active compound of formula I | 5 mg |
| | Lactose | 178 mg |
| | Avicel | 80 mg |
| | Polywachs 6000 | 20 mg |
| | Magnesium stearate | 2 mg |
| 3. | An active compound of formula I | 5 mg |
| | Polyvinylpyrrolidone (mean molecular weight 25,000) | 170 mg |
| | Polyethylene glycol (mean molecular weight 4,000) | 14 mg |
| | Hydroxypropylmethylcellulose | 40 mg |
| | Talc | 4 mg |
| | Magnesium stearate | 2 mg |

Re 3:

The active compound is moistened with a 10% strength aqueous solution of polyvinylpyrrolidone and forced through a sieve of 1.0 mm mesh size, and the granules are dried at 50° C. They are then mixed with polyethylene glycol (mean molecular weight 4,000), hydroxypropylmethylcellulose, talc and magnesium stearate, and the mixture is pressed to give tablets weighing 280 mg.

| Example of coated tablets | | |
| --- | --- | --- |
| 4. | An active compound of formula I | 10 mg |
| | Lactose | 90 mg |
| | Corn starch | 60 mg |
| | Polyvinylpyrrolidone | 6 mg |
| | Magnesium stearate | 1 mg |

The active compound, lactose and corn starch are mixed, moistened with an 8% strength aqueous solution of the polyvinylpyrrolidone, and granulated by passing through a 1.5 mm mesh sieve. The granules are dried of 50° C. and forced through a 1.0 mm sieve. The material thus obtained is mixed with magnesium stearate and the mixture is pressed to form cores. These are coated in a conventional manner with a shell consisting essentially of sugar and talc.

| Capsule formulation | | |
| --- | --- | --- |
| 5. | An active compound of formula I | 5 mg |
| | Magnesium stearate | 2.0 mg |
| | Lactose | 19.3 mg |
| Injection solution | | |
| 6. | An active compound of formula I | 10 mg |
| | Sodium chloride | 9 mg |
| | Distilled water, to make up to 1.0 ml | |

We claim:
1. A compound of the general formula I

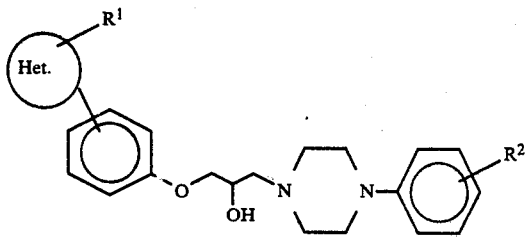

where R[1] is hydrogen, amino or alkyl of 1 to 4 carbon atoms, R[2] is hydrogen, halogen, alkyl of 1 to 4 carbon atoms or alkoxy where alkyl is of 1 to 3 carbon atoms, the phenyl ring can be monosubstituted or disubstituted by R[2], and the heterocyclic structure Het. is triazol-1-yl, imidazol-1-yl, pyrazol-3-yl or isoxazol-3-yl, and its physiologically tolerated addition salts with acids.

2. A compound as set forth in claim 1, where R[1] is hydrogen or amino and R[2] is fluorine, chlorine or methoxy.

3. 1-[4-(1,2,4-Triazol-1-yl)-phenoxy]-3-[4-(4-fluorophenylpiperazin-1-yl]-propan-2-ol.

4. 1-[4-(Imidazol-1-yl)-phenoxy]-3-[4-(4-fluorophenyl)-piperazin-1-yl]-propan-2-ol.

5. 1-[2-(Pyrazol-3-yl)-phenoxy]-3-[4-(2-methoxyphenyl)-piperazin-1-yl]-propan-2-ol.

6. 1-[3-(Pyrazol-3-yl)-phenoxy]-3-[4-(2-methoxyphenyl)-piperazin-1-yl]-propan-2-ol.

7. A pharmaceutical composition having hypotensive, sedative, neuroleptic and broncholytic properties which comprises: an effective amount of a compound of the formula I of claim 1 or its physiologically tolerated acid addition salt and a pharmaceutically acceptable carrier and/or diluent.

* * * * *